(12) United States Patent
Xiqin et al.

(10) Patent No.: US 8,227,743 B2
(45) Date of Patent: Jul. 24, 2012

(54) APPARATUS FOR SELECTING LIGHT OF A SINGLE WAVELENGTH

(75) Inventors: Zhang Xiqin, Singapore (SG); Ting Choon Meng, Singapore (SG)

(73) Assignee: Glucostats System PTE Ltd, Hougang (SG)

( * ) Notice: Subject to any disclaimer, the term of this patent is extended or adjusted under 35 U.S.C. 154(b) by 284 days.

(21) Appl. No.: 11/990,679

(22) PCT Filed: Aug. 17, 2006

(86) PCT No.: PCT/SG2006/000236
§ 371 (c)(1),
(2), (4) Date: Dec. 12, 2008

(87) PCT Pub. No.: WO2007/021251
PCT Pub. Date: Feb. 22, 2007

(65) Prior Publication Data
US 2009/0140130 A1   Jun. 4, 2009

(30) Foreign Application Priority Data

Aug. 18, 2005   (SG) .............................. 200505256-8

(51) Int. Cl.
*H01J 40/14* (2006.01)
*H01J 3/14* (2006.01)
*G06M 7/00* (2006.01)

(52) U.S. Cl. ............... 250/226; 250/221; 250/216
(58) Field of Classification Search ............ 250/226, 250/227.11, 216, 221; 356/402, 416, 418, 356/419, 420; 362/235, 249.01, 249.02, 362/249.03, 249.07, 257, 259, 82, 284, 285, 362/311.01, 311.02, 317, 800, 551, 553–555; 385/25
See application file for complete search history.

(56) References Cited

U.S. PATENT DOCUMENTS

| | | | |
|---|---|---|---|
| 3,697,185 A | 10/1972 | Kassel et al. | |
| 5,165,078 A * | 11/1992 | Hough et al. | 359/233 |
| 5,686,722 A | 11/1997 | Dubois et al. | |
| 6,741,042 B1 * | 5/2004 | Tang | 315/291 |
| 7,113,282 B2 * | 9/2006 | Aguirre et al. | 356/418 |
| 2003/0072333 A1 | 4/2003 | Jacobowitz et al. | |
| 2003/0218723 A1 * | 11/2003 | Yamanaka | 353/30 |
| 2003/0231384 A1 | 12/2003 | Moehler et al. | |

FOREIGN PATENT DOCUMENTS

EP   0 388 082 A2   9/1990
* cited by examiner

*Primary Examiner* — Pascal M Bui Pho
(74) *Attorney, Agent, or Firm* — Husch Blackwell LLP

(57) ABSTRACT

The present invention relates to an arrangement for a selection of a wavelength including a wavelength source for providing a plurality of wavelengths, a wavelength selector for allowing a selection of a desired wavelength from the wavelength source, and a wavelength detector to detect a selected wavelength for subsequent use.

19 Claims, 4 Drawing Sheets

APPARATUS FOR SELECTING LIGHT OF A SINGLE WAVELENGTH

FIELD OF THE INVENTION

The invention relates to an arrangement for providing a selected wavelength from a multi-wavelength source.

BACKGROUND OF THE INVENTION

In the optical absorption technique for blood glucose quantification, the near infrared (NIR) spectral region has been demonstrated to be a highly suitable range. This is because within this range, the water absorption spectrum is relatively minimised, and the peak glucose levels can be readily identified.

Within this range, useful peak glucose absorption wavelengths have been identified at, for example 1200 nm, 1290 nm, 1570 nm, 1650 nm, 2270 nm, 2310 nm, etc. At these optimal values, glucose monitoring may be performed with highly accurate results.

It is desirous for optical absorption techniques for blood glucose monitoring, to obtain and sustain these wavelengths in turn, so that they may be used for blood glucose monitoring purposes of a patient.

Presently, the Acousto-Optic Tuneable Filter (AOTF) is used to generate the NIR spectral region for this purpose. The AOTF setup is not only expensive and bulky, the use of acousto optics for selection of wavelengths is highly dependent on the temperature. This is because a change in temperature would bring about a change in the velocity of sound, which in turn influences the wavelengths generated. It can be appreciated that the stability of each tuned wavelength is also a concern.

There is therefore a need to provide an economical means for generating and obtaining optimal wavelength values for reliable and accurate glucose monitoring

SUMMARY OF THE INVENTION

According to an aspect of the present invention, there is provided an arrangement for a selection of a wavelength, including a wavelength source for providing a plurality of wavelengths, a wavelength selector for allowing a selection of a desired wavelength from the wavelength source and a wavelength detector to detect a selected wavelength for subsequent use.

Preferred aspects of the present invention are in accordance with the subject matter of subsidiary claims of the appended claims, and are imported into the description by reference.

Preferably, the wavelength source is a source disc further including a plurality of laser diodes, each laser diode configured to emit a single wavelength.

Still preferably, the laser diodes are positioned along a periphery of the source disc.

In a first embodiment, the source disc is rotatable.

Preferably, the wavelength selector is a selector disc further including an aperture, said aperture sized and positioned to allow a wavelength from a laser diode therethrough.

In a second embodiment, the selector disc is rotatable.

Preferably, the wavelength detector is a detector disc having at least one wavelength detector along the periphery of said disc positioned to detect a selected wavelength of the wavelength source.

Still preferably, wherein the wavelength detector is at least one fibre optic head.

In a first operating mode, each laser diode is aligned with a corresponding fibre optic head, and a wavelength is selected by rotating the selector disc so that the aperture is co-axially aligned with the laser diode emitting a selected wavelength, to allow the selected wavelength therethrough for detection by the corresponding fibre optic head.

In a second operating mode, the aperture of the selector disc is aligned with a fibre optic head, and a wavelength is selected by rotating the source disc so that the laser diode emitting a selected wavelength is co-axially aligned with the aperture, to allow the selected wavelength therethrough for detection by the corresponding fibre optic head.

Preferably, in a first operating mode, the selector disc is mounted on an axle.

In a first preferred embodiment, the selector disc is rotated manually about the axis to select a wavelength.

Preferably, the axle includes a biasing means, to retain a rotated position of the selector disc once a wavelength has been selected.

In a second preferred embodiment, the rotation is automated.

Preferably, the selector is coupled to a stepper motor, said stepper motor programmed to rotate the selector disc to a relevant angle for the selection of a wavelength.

Still preferably, the motor further includes a timer, to interrupt the rotation for a period of time prior to rotating to a next angle.

In a second operating mode, the source disc is mounted on an axle.

In a third preferred embodiment, the source disc is rotated manually about the axis to select a wavelength.

Preferably, the axle includes a biasing means, to retain a rotated position of the source disc once a wavelength has been selected.

In a fourth preferred embodiment, the rotation is automated.

Preferably, the source disc is coupled to a stepper motor, said stepper motor programmed to rotate the source disc to a relevant angle for the selection of a wavelength.

Still preferably, the motor further includes a timer, to interrupt the rotation for a period of time prior to rotating to a next angle.

In an embodiment, the fibre optic heads are directed to a patient's region of diagnosis, and thereafter to a photo diode for signal processing.

DESCRIPTION OF FIGURES

In order that the present invention might be more fully understood, embodiments of the invention will be described, by way of example only, with reference to the accompanying drawings, in which.

In each of the embodiments, the same reference numerals have been used for similar components, merely for ease of understanding the specification.

The attached drawings are not necessarily drawn to scale.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to a person who is ordinarily skilled in the art that the present invention may be practised without these specific details. In other instances, well known methods, procedures, components, and features have not been described in detail so as not to unnecessarily obscure aspects of the present invention.

Figure 1:
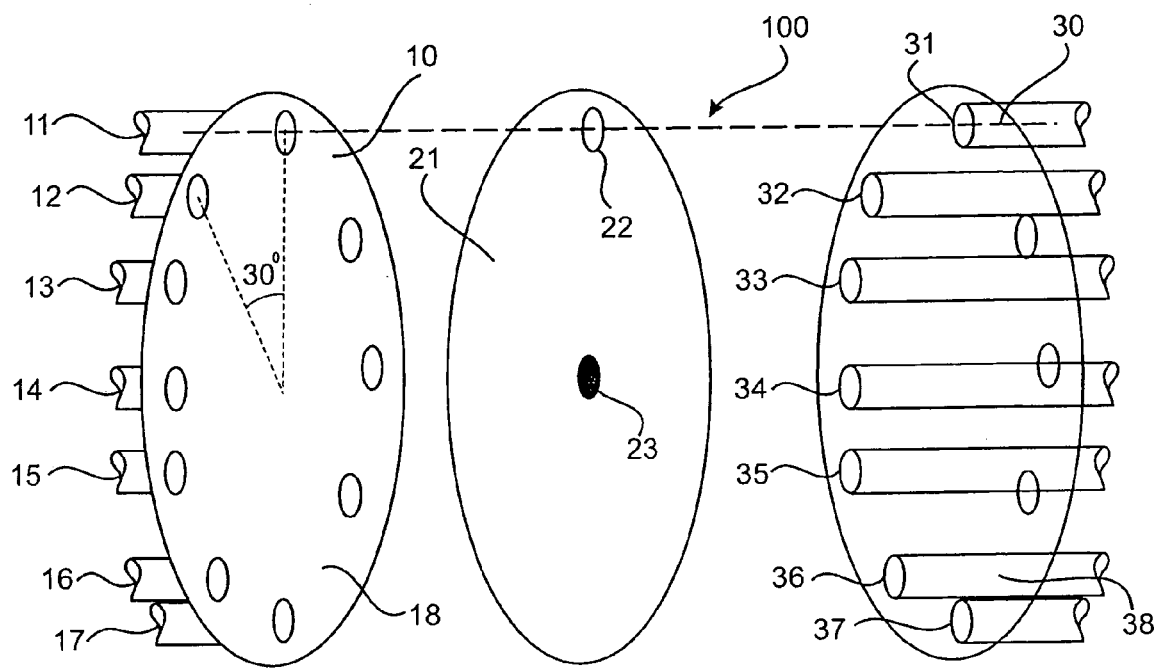
FIG. 1 shows the arrangement of the invention according to a first operating mode of the invention.

FIG. 1 shows the arrangement 100 for providing a selected wavelength according to a first embodiment of the invention.

The arrangement 100 includes a wavelength source 10, a wavelength selector 20 and a wavelength detector 30. The purpose of the arrangement is to allow a user to select a desired wavelength from a multi-wavelength source. This desired wavelength is then directed to a selected diagnostic region of a patient, for, as described in the following paragraphs, blood glucose monitoring.

Wavelength Source

The wavelength source 10 is shown having a plurality of laser diodes, or light emitting diodes 11-17, arranged along or near the periphery of a source disc 18. The source disc may be rotatable and will be explained in a second operating mode of the invention. Each laser diode is configured to emit a single wavelength, of the useful glucose peak absorption wavelength as previously described. For example, laser diode 11 is configured to transmit an optimal wavelength of 1200 nm, and so on. The laser diodes are uniformly spaced apart, and the rotational angle between a first laser diode and the next, is dependent on the number of wavelengths (or channels) that is desired. As seen in FIG. 1, 12 channels are used, and therefore there are 12 laser diodes each emitting a single optimal wavelength. In this situation, the rotational angle between a first laser diode 11 and a second laser diode 12 is 30°. However, where a 24-channel arrangement is desired, then the rotational angle between each of the laser diode is 15°. As can be appreciated, there are limitless possibilities of this arrangement to suit the number of channels.

Wavelength Detector

The wavelength detector 30 consists of a plurality of fibre optic heads 31-37 on a detector disc 38. The arrangement of the fibre optic heads on the detector disc 38 is identical to the arrangement of the laser diodes on the source disc 18. The relationship of the wavelength source and the wavelength detector will be explained later in two operating modes.

Selector

The selector 20 is in the form of a selector disc 21 that may be rotatable and is positioned between the wavelength source 10 and the wavelength detector 30. The selector disc 21 has an aperture 22, sized and positioned to allow a selected beam from a laser diode therethrough, for detection in a corresponding fibre optic head.

Operating Modes

First Operating Mode

In a first operating mode, the detector disc 38 and the source disc 18 are fixed in relation to each other. Each fibre optic head is positioned to be linearly aligned with a particular laser diode. As seen in FIG. 1, laser diode 11 is in alignment with fibre optic head 31, and laser diode 12 is in alignment with fibre optic head 32, and so on. The source disc 18 and the detector disc 38 are fixed in relation to each other, so that a particular laser diode will always be in alignment with its corresponding fibre optic head. For example, laser diode 11 will be detected by fibre optic head 31. Therefore, as can be appreciated, when a 12-channel source is adopted, then the fibre optic heads are 30° apart from each other. However, where a 24-channel source is required, then the laser diodes and the fibre optic heads are each spaced 15° from each other.

Therefore, when a particular wavelength is desired, the selector 20 is rotated until the aperture 22 is co-axially aligned between the selected wavelength source and the corresponding fibre optic head. As only one aperture is provided on the selector 20, it is to be appreciated that only one wavelength is allowed therethrough at each time. All other wavelengths will not be detected by the corresponding fibre optic head as they are obstructed by the selector disc 21. Therefore, at any one time, only one wavelength is allowed therethrough for detection.

For example, as seen in FIG. 1 in a first operating mode, the source disc 18 and the detector disc 38 are fixed in relation to one another, so that when the aperture 22 is rotated about an axle 23 to be aligned with laser diode 11 transmitting 1200 nm, then this wavelength is transmitted therethrough, and detected by optical fibre head 31. All other wavelengths will not be transmitted therethrough as they are absorbed by the selector. Therefore, it can be appreciated that the selector allows a user to 'select' a desired wavelength for use in blood glucose monitoring.

In an embodiment, a biasing means (not shown in the figures) is provided to maintain the position of the selector, once a desired wavelength is selected through rotation of the selector. The biasing means may be in the form of a releasable clip, so that when rotation is desired, the clip is released, so that the rotatable selector disc 21 may be rotated about the axle 23. Once a desired rotation is obtained, the clip is then locked so that the position of the selector disc is maintained, and the desired wavelength is obtained and detected by the corresponding fibre optic head.

Figure 2:
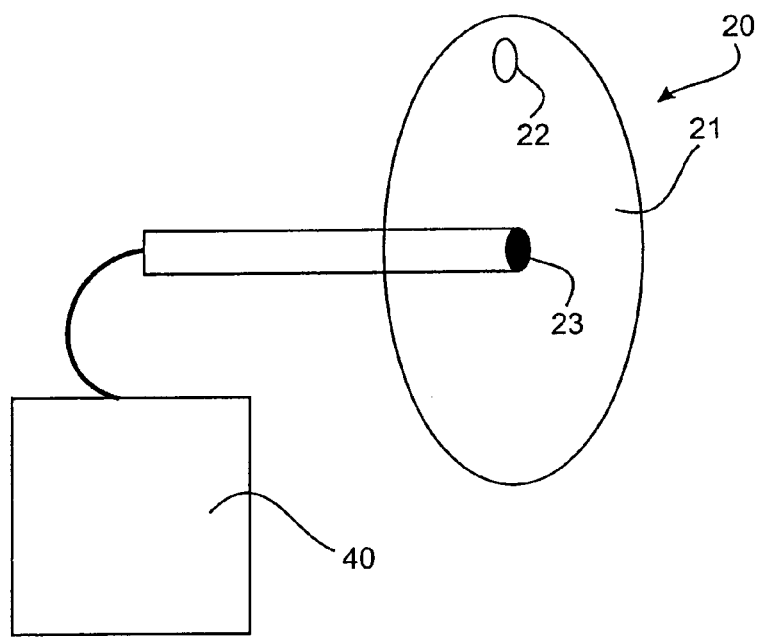
FIG. 2 shows a selector in a second embodiment of the invention.

In another embodiment as seen in FIG. 2, the rotation of the selector 20 is automated. In this embodiment, the selector 20 is coupled to a stepper motor 40, and may be programmed so as to rotate to each relevant angle for the selection of a wavelength. For example, where there are 12 laser diodes used (i.e. 12-channels), then a 30° rotation is required to select a second wavelength from the first wavelength. A timer may further be provided, so that the rotation may be interrupted for a period of time, prior to rotating to a next angle (to select a next wavelength). This interruption is advantageous as the time lag allows data sampling to be performed based on the readings obtained for each selected wavelength.

When in use, the wavelengths detected are transmitted through an optical head. The fibre optic heads are coupled using a fibre coupler, and directed onto a patient's region of diagnosis and thereafter to a common photo diode for signal processing through a signal processor.

Figure 3:
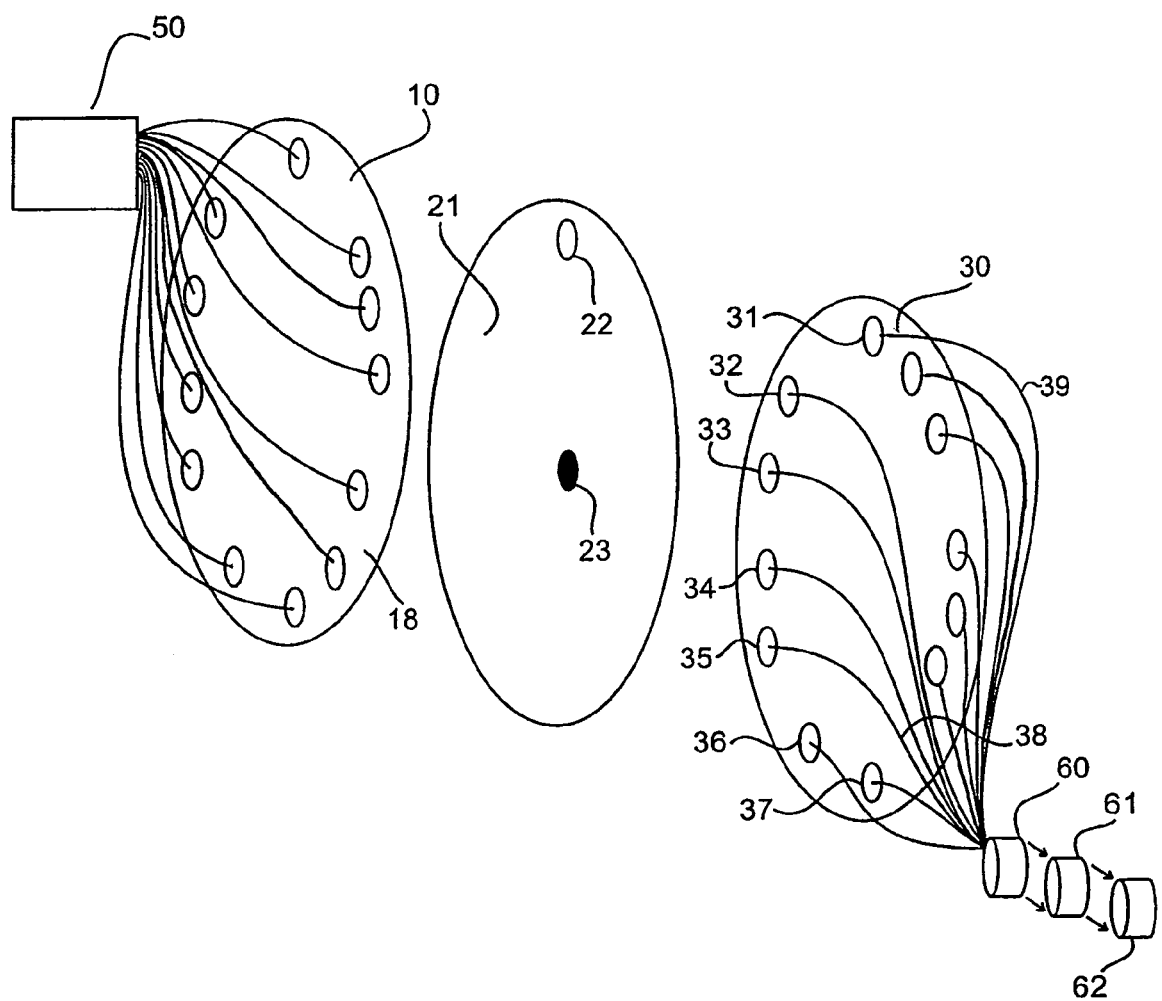
FIG. 3 shows the arrangement when in use for the purposes of blood glucose monitoring.

FIG. 3 shows the whole arrangement in use, showing the wavelength source 10, the selector 20 and the wavelength detector 30. The laser diodes (or light emitting diodes) are powered by a common power supply 50. When a desired wavelength is selected, for example, 1290 nm, this wavelength is then detected by its corresponding detector, or fibre optic head. The fibre optic wires 39 are coupled using a fibre coupler so that the required wavelength may be directed at a specified monitoring area 60. In this area, a patient's region of diagnosis for e.g. a fingernail may be placed, so that the selected wavelength may penetrate the fingernail and be subsequently directed to a photodiode 61 for subsequent signal processing through a signal processor 62. Once the readings are obtained, the selector 20 is then rotated to a next desired wavelength for signal processing. The rotation may be performed manually, or this may be automated using a stepper motor, as previously described.

Second Operating Mode

Figure 5:
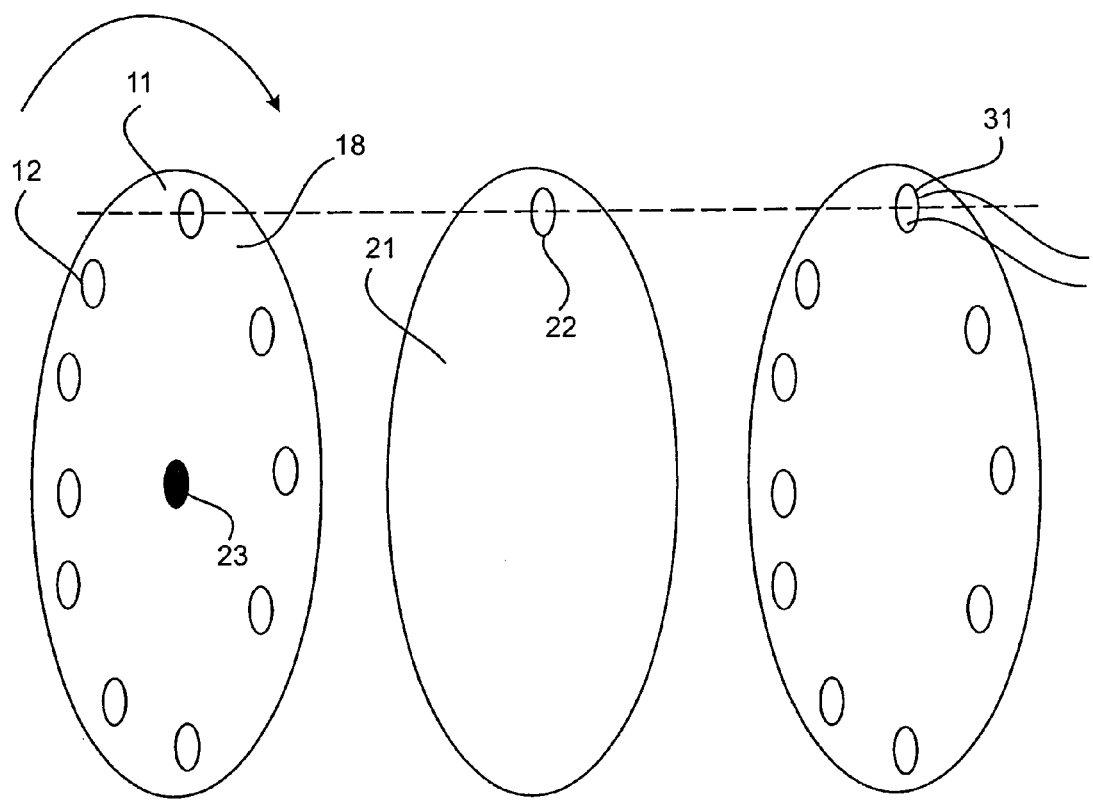
FIG. 5 shows the arrangement of the invention according to a second operating mode of the invention.

In a second operating mode, the selector disc 21 and the detector disc 38 are fixed in relation to each other. In this operating mode, as seen in FIG. 5, the source disc 18 is rotatable about an axis 23. In this operating mode, the wavelength detector may have only one fibre optic head 31, positioned to be linearly aligned with the aperture 22 of the selector disc 21.

In use, the source disc 18 is rotated till a first laser diode 11 is linearly aligned with the aperture 22 of the selector disc 21. In this position, a first wavelength may be detected by the fibre optic head 31. To shift to a next wavelength, the source disc 18 is rotated until the second laser diode 12 is linearly aligned with the aperture 22 and the fibre optic head 31. The source disc 18 may be rotated manually, or automated, as previously described. In this manner, a wavelength may also be selected from a multiple source.

Therefore, it can be appreciated that the selector allows a user to 'select' a desired wavelength for use in blood glucose monitoring.

Figure 4:
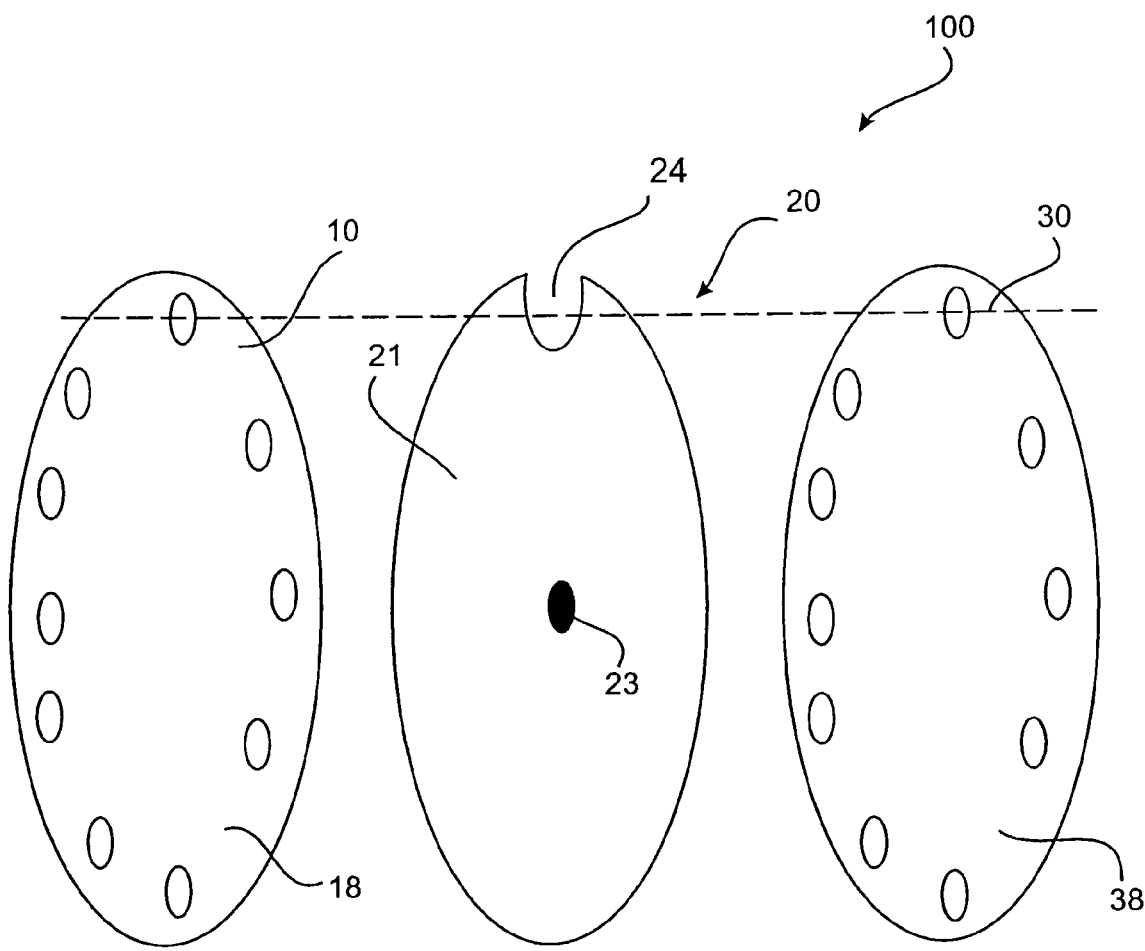
FIG. 4 shows the selector in a third embodiment of the invention

In another embodiment of the selector as seen in FIG. 4, the aperture is in the form of a notch 24, dimensioned to allow a selected wavelength therethrough.

The embodiments of the invention have been advanced by way of example only, and modifications are possible within the scope of the invention as defined by the appended claims.

The invention claimed is:

1. An arrangement for a selection of a wavelength including:
   a wavelength source for providing a plurality of wavelengths, wherein the wavelength source is a source disc including a plurality of laser diodes, each of which is configured to emit a single wavelength;
   a wavelength selector separate from said wavelength source for allowing a selection of a single wavelength from the wavelength source, said wavelength selector comprising a rotatable disc having only one aperture to allow therethrough only the single wavelength at one time from the plurality of wavelengths; and
   a wavelength detector to detect the single wavelength for subsequent use, said wavelength source being fixed in relation to said wavelength detector and allowing the alignment of the aperture of the wavelength with said source disc and said wavelength detector at the same time to allow the single wavelength through at one time to said wavelength detector,
   wherein, in a first operating mode, each laser diode is aligned with a corresponding fibre optic head, and a wavelength is selected by rotating the selector disc so that the aperture is co-axially aligned with the laser diode emitting a selected wavelength, to allow the single wavelength therethrough for detection by the corresponding fibre optic head, and
   wherein, in a second operating mode, the aperture of the selector disc is aligned with a corresponding fibre optic head, and a single wavelength is selected by rotating the source disc so that the laser diode emitting the single wavelength is co-axially aligned with the aperture, to allow the single wavelength therethrough for detection by the corresponding fibre optic head.

2. An arrangement for a selection of a wavelength according to claim 1, wherein the laser diodes are positioned along a periphery of the source disc.

3. An arrangement for a selection of a wavelength according to claim 1, wherein the wavelength detector is a detector disc having at least one wavelength detector along the periphery of said disc positioned to detect a single wavelength of the wavelength source.

4. An arrangement for a selection of a wavelength according to claim 1, wherein the wavelength detector is at least one of the fibre optic head.

5. An arrangement for a selection of a wavelength according to claim 4, wherein the fibre optic heads of the wavelength detector are directed to a patient's region of diagnosis, and thereafter to a photo diode for signal processing.

6. An arrangement for a selection of a wavelength according to claim 1 wherein the selector disc is mounted on an axle.

7. An arrangement for a selection of a wavelength according to any claim 6, wherein the axle includes a biasing means, to retain a rotated position of the selector disc once a wavelength has been selected.

8. An arrangement for a selection of a wavelength according to claim 6, wherein the axle includes a biasing means, to retain a rotated position of the source disc once the single wavelength has been selected.

9. An arrangement for a selection of a wavelength according to claim 1, wherein the selector disc is rotated manually about the axis to select a wavelength.

10. An arrangement for a selection of a wavelength according to claim 1, wherein the rotation of the selector disc is automated.

11. An arrangement for a selection of a wavelength according to claim 1, wherein the selector is coupled to a stepper motor, said stepper motor programmed to rotate the selector disc to a relevant angle for the selection of the single wavelength.

12. An arrangement for a selection of a wavelength according to claim 11, wherein the motor further includes a timer, to interrupt the rotation of the selector disc for a period of time prior to rotating to a next angle.

13. An arrangement for a selection of a wavelength according to claim 1, wherein the source disc is mounted on an axle.

14. An arrangement for a selection of a wavelength according to claim 1, wherein the source disc is rotated manually about the axis to select the single wavelength.

15. An arrangement for a selection of a wavelength according to claim 1, wherein the rotation of the source disc is automated.

16. An arrangement for a selection of a wavelength according to claim 1, wherein the source disc is coupled to a stepper motor, said stepper motor programmed to rotate the source disc to a relevant angle for the selection of the single wavelength.

17. An arrangement for a selection of a wavelength according to claim 16, wherein the motor further includes a timer, to interrupt the rotation of the source disc for a period of time prior to rotating to a next angle.

18. An arrangement for a selection of a wavelength including:
- a wavelength source for providing a plurality of wavelengths, wherein the wavelength source is a source disc including a plurality of laser diodes, each of which is configured to emit a single wavelength;
- a rotatable wavelength selector alignable with said wavelength source for allowing a selection of a desired single wavelength from the wavelength source, said wavelength selector comprising a disc having only one aperture to allow therethrough only the single wavelength, said wavelength source being separate from each other; and
- a wavelength detector to detect the desired single wavelength for subsequent use, said wavelength detector fixed to said wavelength selector for following rotation, whereby said wavelength selector is rotated and aligned with said wavelength source to allow the desired single wavelength to pass through said wavelength selector to said wavelength detector,
- wherein, in a first operating mode, each laser diode is aligned with a corresponding fibre optic head, and a wavelength is selected by rotating the selector disc so that the aperture is co-axially aligned with the laser diode emitting a selected wavelength, to allow the single wavelength therethrough for detection by the corresponding fibre optic head, and
- wherein, in a second operating mode, the aperture of the selector disc is aligned with a corresponding fibre optic head, and a single wavelength is selected by rotating the source disc so that the laser diode emitting the single wavelength is co-axially aligned with the aperture, to allow the single wavelength therethrough for detection by the corresponding fibre optic head.

19. An arrangement for a selection of a wavelength including:
- a wavelength source for providing a plurality of wavelengths, wherein the wavelength source is a rotatable source disc including a plurality of laser diodes, each of which is configured to emit a single wavelength and rotatable with the source disc;
- a wavelength detector to detect the single wavelength for subsequent use, said wavelength source being rotatable to allow the alignment of said source disc and said wavelength detector to allow the single wavelength therethrough to said wavelength detector; and
- a wavelength selector for allowing selection of the single wavelength from the wavelength source, said wavelength selector comprising a disc having only one aperture to allow therethrough only a single wavelength from the plurality of wavelengths, said wavelength detector being between the wavelength source and the wavelength detector,
- wherein, in a first operating mode, each laser diode is aligned with a corresponding fibre optic head, and a wavelength is selected by rotating the selector disc so that the aperture is co-axially aligned with the laser diode emitting a selected wavelength, to allow the single wavelength therethrough for detection by the corresponding fibre optic head, and
- wherein, in a second operating mode, the aperture of the selector disc is aligned with a fibre optic head, and a single wavelength is selected by rotating the source disc so that the laser diode emitting the single wavelength is co-axially aligned with the aperture, to allow the single wavelength therethrough for detection by the corresponding fibre optic head.

* * * * *